(12) United States Patent
Farley et al.

(10) Patent No.: US 8,740,908 B2
(45) Date of Patent: Jun. 3, 2014

(54) BONE COLLECTION SYSTEM

(75) Inventors: Daniel K. Farley, Traverse City, MI (US); Christper T. Martin, Empire, MI (US); Steve Nowak, Traverse City, MI (US); Stephanie Zalucha, Williamsburg, MI (US)

(73) Assignee: Thompson MIS, Salem, NH (US)

( * ) Notice: Subject to any disclaimer, the term of this patent is extended or adjusted under 35 U.S.C. 154(b) by 0 days.

(21) Appl. No.: 13/287,741

(22) Filed: Nov. 2, 2011

(65) Prior Publication Data

US 2012/0109227 A1 May 3, 2012

Related U.S. Application Data

(60) Provisional application No. 61/409,338, filed on Nov. 2, 2010.

(51) Int. Cl.
*A61B 17/56* (2006.01)

(52) U.S. Cl.
USPC ........... 606/86 R; 604/317; 210/396; 210/499

(58) Field of Classification Search
USPC ................. 606/53, 79, 80, 84, 86 R, 87, 914; 623/23.51, 23.61, 23.63, 16.11; 15/104.001, 104.03, 104.05, 104.16; 210/391, 396, 407, 499; 422/534; 604/317, 416
See application file for complete search history.

(56) References Cited

U.S. PATENT DOCUMENTS

| | | | |
|---|---|---|---|
| 2,226,317 A | * | 12/1940 | Myers ........................... 241/166 |
| 3,414,925 A | * | 12/1968 | Stavros .................... 15/104.001 |
| 4,015,602 A | * | 4/1977 | Nelson et al. ................. 604/236 |
| 5,114,240 A | * | 5/1992 | Kindt-Larsen et al. ....... 366/129 |
| 5,766,134 A | | 6/1998 | Lisak |
| 6,022,354 A | | 2/2000 | Mercuri |

(Continued)

FOREIGN PATENT DOCUMENTS

WO    WO 03/073945 A1    9/2003

OTHER PUBLICATIONS

Patent Cooperation Treaty, PCT Notification of Transmittal of the International Search Report and the Written Opinion of the International Searching Authority, or the Declaration, in International application No. PCT/US2011/058946, dated Feb. 21, 2012.

(Continued)

*Primary Examiner* — Todd Manahan
*Assistant Examiner* — Marcela I Shirsat
(74) *Attorney, Agent, or Firm* — McAndrews, Held & Malloy, Ltd.

(57) ABSTRACT

A bone collection system includes a plunger, a tube, and a manifold. The plunger has a bore therethrough, an insertion portion, and an inlet that accepts material being harvested from a patient. The insertion portion includes a filter to prevent passage of bone fragments. The tube accepts the insertion portion, defining a first and a second chamber of the tube. The filter separates the first and second chambers of the tube. The manifold is accepted by the tube, and has an outlet accepted by a suction source. The inlet of the plunger is in fluid communication with the first chamber, the first and second chambers are in fluid communication through the filter, and the second chamber is in fluid communication with the outlet. Material being harvested is drawn through the bone collection system, and bone fragments of the desired size collected in the first chamber.

17 Claims, 12 Drawing Sheets

(56) References Cited

U.S. PATENT DOCUMENTS

| | | | |
|---|---|---|---|
| 6,852,127 B2* | 2/2005 | Varga et al. | 623/17.11 |
| 8,246,572 B2* | 8/2012 | Cantor et al. | 604/60 |
| 2002/0119417 A1* | 8/2002 | Ashman | 433/90 |
| 2002/0177824 A1 | 11/2002 | Hajianpour | |
| 2006/0052760 A1 | 3/2006 | Batzdorf | |
| 2006/0106353 A1 | 5/2006 | Geneve | |
| 2007/0225665 A1* | 9/2007 | Perez-Cruet et al. | 604/317 |
| 2013/0006366 A1* | 1/2013 | Farley et al. | 623/17.16 |

OTHER PUBLICATIONS

PCT, Notification Concerning Transmittal of International Preliminary Report on Patentability, in International application No. PCT/US2011/058946, dated May 15, 2013.

* cited by examiner

BONE COLLECTION SYSTEM

CROSS-REFERENCE TO RELATED APPLICATION

The present application makes reference to, claims priority to, and incorporates in its entirety U.S. Provisional Patent Application 61/409,338, entitled "Bone Collection System," filed Nov. 2, 2010.

STATEMENT REGARDING FEDERALLY SPONSORED RESEARCH OR DEVELOPMENT

None.

BACKGROUND OF THE INVENTION

Certain embodiments of the present invention relate to systems and methods for collecting bone material and providing bone graft material to spaces proximate to spinal implants, for example, to be used in connection with spinal fusion. Examples of certain bone collection devices are further discussed in U.S. Pat. No. 7,758,556, the content of which is hereby incorporated by reference in its entirety.

Spinal fusion is a surgical procedure that fuses two or more vertebrae together using bone graft materials supplemented with devices. Spinal fusion may be performed for the treatment of chronic neck and/or back pain, trauma, and neoplasms. Spinal fusion can be used to stabilize and eliminate motion of vertebrae segments that may be unstable, or move in an abnormal way, that can lead to discomfort and pain. Spinal fusion may be performed to treat injuries to the vertebrae, degeneration of spinal discs, abnormal spinal curvature, and/or a weak or unstable spine.

Spinal fusion generally requires a graft material, usually bone material, to fuse the vertebrae together. The bone graft material can be placed over the spine to fuse adjacent vertebrae together. Alternatively, a device may be positioned between the vertebrae being fused and filled with the bone graft material, or bone graft material may be used to surround a portion or portions of the device. Such a device can include holes that allow the vertebrae and the graft material to grow together to provide fusion, with the cage supporting the weight of the vertebrae while the fusion is occurring. Most of these cages are limited to only a few cubic centimeters of bone graft material thus limiting the fusion area achieved. Because the fusion mass is under pressure, fusion can be promoted. The disc space height can be restored, taking pressure off of the nerves. The spine alignment, foraminal height, and canal diameter can be restored. In some cases the graft can be placed with minimal disruption of muscles and ligaments using minimally invasive approaches to the spine, thus preserving the normal anatomical integrity of the spine. Other interbody device assemblies are also presently known. These include those disclosed in U.S. patent application Ser. No. 11/623,356, filed Jan. 16, 2007, titled "Minimally Invasive Interbody Device," and Ser. No. 11/932,175, filed Oct. 31, 2007, titled "Minimally Invasive Interbody Device Assembly," which are hereby incorporated by reference in their entirety.

Typically, the bone graft material is autogenous bone material taken from the patient, or allograft bone material harvested from a cadaver. Synthetic bone material can also be used as the graft material. Generally, the patient's own bone material offers the best fusion material since it offers osteoinductive, osteoconductive, and osteogenesis properties. Known bone fusion materials include iliac crest harvest from the patient, bone graft extenders, such as hydroxyapetite and demineralized bone matrix, and bone morphogenic protein.

During most spinal surgical procedures, a drill is used to take bone away to allow for decompression of the spinal nerves and/or the spinal cord. Bone is also drilled from the spine to create a 'decorticated' fusion bed. Typically, this bone is removed by suction.

Minimally invasive surgical procedures have been devised in an attempt to preserve normal anatomical structures during spinal surgery. Many known procedures for spinal fusion, however, still are more invasive than desired. Additonally, many known procedures do not provide the level of control over the collection, delivery, and placement of the bone graft material as could be desired.

It is therefore one object of the present invention to provide a bone collection and bone graft delivery system that reduces approach related morbidity, allows for improved bone graft collection and placement, and/or provides improved control of the delivery and/or placement of bone graft material.

BRIEF SUMMARY OF THE INVENTION

These and other objects of the invention are achieved in a bone collection system that includes a plunger, a tube, and a manifold. The plunger has a bore therethrough, an insertion portion, and an inlet. The inlet is configured to accept material being harvested from a patient. Also, the insertion portion includes a filter configured to prevent passage of a desired size of bone fragment. The tube is configured to accept the insertion portion of the plunger wherein a first and a second chamber of the tube are defined. The first and second chambers of the tube are separated by the filter of the plunger. The manifold is configured to be accepted by the tube. The manifold has an outlet configured to be accepted by an external suction source. The inlet of the plunger is in fluid communication with the first chamber, the first and second chambers are in fluid communication through the filter, and the second chamber is in fluid communication with the outlet. Material being harvested from a patient may be drawn through the bone collection system, and bone fragments of the desired size collected in the first chamber. The stylette is configured to eject collected bone fragments out of one end of the tube, and the cleaner includes posts sized to remove material from the holes of the filter.

In certain embodiments, the filter of the plunger includes a screen and a screen cleaner adapted for cleaning the screen. The screen includes a plurality of holes, and the screen cleaner includes a plurality of posts sized and configured to be accepted by the plurality of holes of the screen.

In certain other embodiments, the filter of the plunger includes a screen including a plurality of holes, and the manifold includes a screen cleaner portion. The screen cleaner portion, which may be located on a bottom portion of the manifold, includes a plurality of posts sized and configured to be accepted by the plurality of holes of the screen. Further, the manifold may be slidingly accepted by the shaft of the plunger so that it and the screen may be slid toward each other. In certain embodiments, the manifold may include a manifold opening that is slidingly accepted by the plunger.

Further, in certain embodiments, the system includes a stylette configured to aid in the removal of material from the tube. The stylette includes a head configured to be slidingly accepted by the tube. The head of the stylette and/or the insertion portion of the plunger may include a tapered leading edge. Alternatively or additionally, the tube may include a removable base for maintaining the material being harvested from the patient in the first chamber.

Also, in certain embodiments, the tube may include a tube outlet proximal to an end of the tube. The tube outlet may have a reduced diameter compared to the diameter of the tube.

Certain embodiments of the present invention provide a system for collecting and delivering bone material including a bone collection device, a spacer, a funnel and a stylette. The spacer is configured for implantation in an intervertebral space. The funnel is configured for delivery of bone graft material to a space proximate to the spacer. The funnel includes a tube end configured to be couple to a tube outlet of the bone collection device. The stylette is configured to force collected bone fragments out of the tube outlet, through the funnel, and to the space proximate to the spacer.

In certain embodiments, the funnel includes a spacer end opposite the tube end of the funnel. The spacer end of the funnel includes a feature, such as a notch, adapted for aligning the spacer end of the funnel with the spacer.

In certain embodiments, the funnel and the tube include substantially similar sized inner diameters. Thus, a single stylette may be slidingly accepted by both the funnel and the tube.

DETAILED DESCRIPTION

Figure 1:
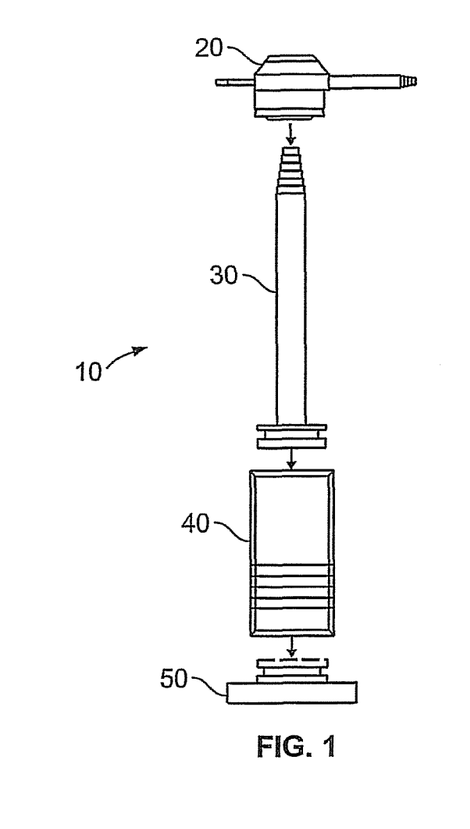
FIG. 1 illustrates an exploded view of a bone collection system formed in accordance with an embodiment of the present invention.
Figure 2:
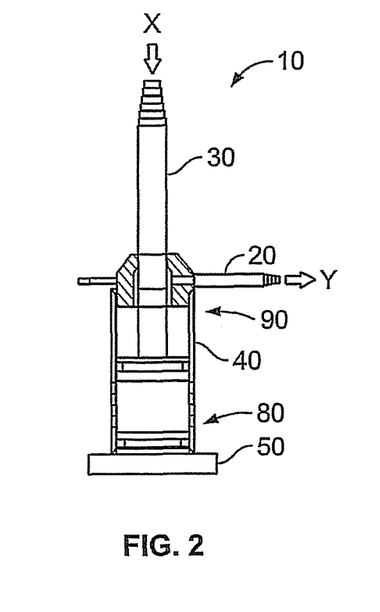
FIG. 2 illustrates a side sectional view of the bone collection system of FIG. 1 in an assembled condition.

FIG. 1 illustrates an exploded view of a bone collection system 10 formed in accordance with an embodiment of the present invention, and FIG. 2 illustrates a side sectional view of the bone collection system 10 in an assembled condition. As seen in FIGS. 1 & 2, the bone collection system 10 includes a manifold 20, plunger 30, tube 40, and base 50. The bone collection system 10 may also include a stylette 60 and a cleaner 70 (see FIGS. 10-12). Various components of the bone collection system 10 may be made of sterilizeable plastic and/or stainless steel, to permit the components to be sterilized and re-used.

Before addressing individual components, a brief summary of the general operation of an embodiment of the present invention is provided. The bone collection system 10 can be used to collect bone that is harvested from a location within a patient, such as bone drilled away to allow for decompression of the spinal nerves and/or the spinal cord and/or bone drilled from the spine to create a 'decorticated' fusion bed. To use the assembled bone collection system, an external suction source, such as a pump, is coupled to an outlet of the manifold 20, such that suction is applied to a top portion of the tube 40 from the external suction source at Y. The plunger 30 is coupled to a collection device that removes bone and other material, such as blood, from a bone harvesting site in a patient. The material is collected from the patient through the collection device and to the plunger 30 at X. The material is then suctioned through a bore in the plunger 30 into a bottom portion of the tube 40. From the bottom portion of the tube 40, the material is drawn, under suction, through a screen or filter of the plunger into an upper portion of the tube 40. The screen or filter is configured so that re-usable bone fragments are collected in the bottom portion of the tube 40, and blood and other waste material is allowed through the screen or filter. The blood and other waste material is drawn through the screen or filter into a top portion of the tube 40, from where it is suctioned out of the tube 40 by the external suction source. The bone fragments remaining in a bottom portion of the tube may then be used as part of a bone graft addition, such as surrounding a spinal implant.

Figure 3:
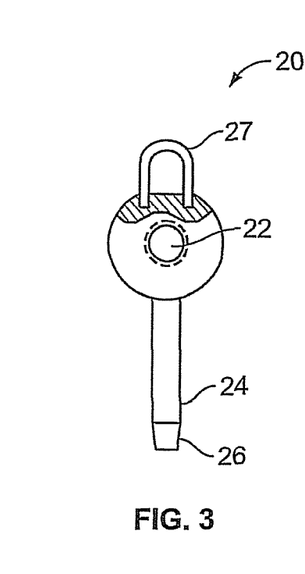
FIG. 3 provides a top view of a manifold formed in accordance with an embodiment of the present invention.
Figure 4:
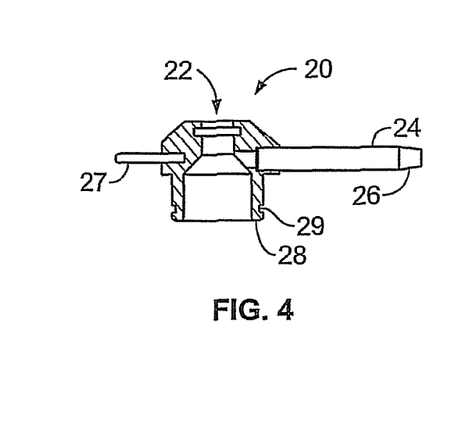
FIG. 4 provides a side sectional view of the manifold of FIG. 3.

Turning now to embodiments of various components of the illustrated bone collection system 10, FIG. 3 provides a top view of a manifold 20 formed in accordance with an embodiment of the present invention, and FIG. 4 provides a side sectional view of the manifold 20. The manifold 20 includes a bore 22, outlet 24, handle 27, and insertion portion 28. The bore 22 is configured to accept the plunger 30, and may further include an additional larger bore or groove (or a plurality of such bores or grooves) sized to accept an O-ring or other seal (not shown) (or a plurality of such O-rings or seals) to help seal any gap between the bore 22 and the outer surface of the plunger 30 and to help minimize or prevent any leakage that could impair the suction of material through the bone collection system 10. In the illustrated embodiment, the outlet 24 is generally tubular and includes a tip 26 that is adapted to accept tubing or hose to connect the outlet 24 to an external suction source, such as a pump. For example, the tip 26 may be tapered to facilitate insertion into tubing or a hose, and/or include grooves or ridges to help retain the tip 26 inside the tubing or hose once inserted. The handle 27 is configured to provide a convenient location for grasping and manipulating the manifold 20.

In the illustrated embodiment, the insertion portion 28 is configured to allow the manifold 20 to be releasably and sealably secured to the tube 40. The insertion portion 28 is generally cylindrically shaped and sized so that its outer diameter is accepted by the inner diameter of the tube 40. The insertion portion includes a groove 29 that accepts an O-ring or seal (not shown) so that the insertion portion 28 and tube 40 provide a fluid-tight fit to minimize or prevent leakage that could impair the suction of material through the bone collection system 10. In alternate embodiments, the insertion portion of the manifold and tube may be for example, snappably engageable, or, as another example, threadedly engageable.

Figure 5:
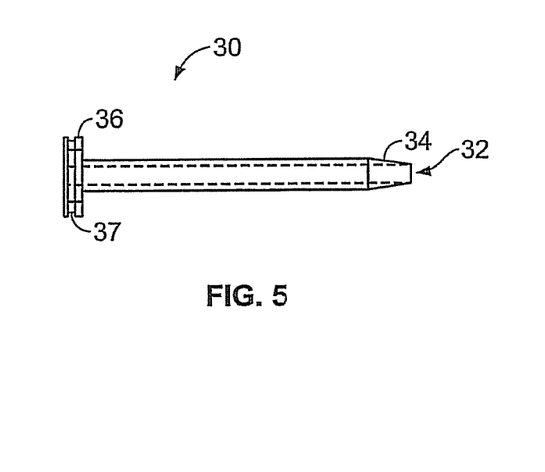
FIG. 5 illustrates a side view of a plunger formed in accordance with an embodiment of the present invention.
Figure 6:
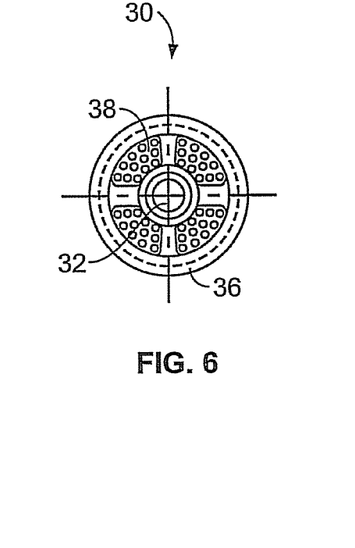
FIG. 6 provides a top view of the plunger of FIG. 5.

FIG. 5 illustrates a side view of a plunger 30 faulted in accordance with an embodiment of the present invention, and FIG. 6 provides a top view of the plunger 30. The plunger 30 includes a bore 32, a tip 34, and an insertion portion 36. The bore 32 extends throughout the plunger 30 and provides a conduit for fluid communication between a harvest site in a patient (for example, via a collection device) and a bottom portion of the tube 40 when the plunger 30 is positioned in the tube 40 during a bone collection procedure. The tip 34 is adapted for cooperation with, for example, tubing or a hose to place the bore 32 in fluid communication with a collection device. For example, the tip 34 may be tapered to facilitate insertion into tubing or a hose, and/or include grooves or ridges to help retain the tip 34 inside the tubing or hose once inserted.

The insertion portion 36 of the plunger 30 is configured to be slidingly accepted by the tube 40. In certain embodiments, the insertion portion may be sealably accepted, and in such embodiments the insertion portion 36 may include a groove 37 that accepts an O-ring or seal (not shown) to prevent or minimize any leakage between the outer surface of the insertion portion 36 and the inner surface of the tube 40, and helping to allow the outlet of the manifold to be in direct fluid communication with one chamber of the tube but not in direct fluid communication with the inlet or the other chamber of the tube. The insertion portion 36 also includes a screen 38. The screen 38 is an example of a filter for separating usable bone fragments from other material, such as blood, that is collected and suctioned from the harvest site. In the illustrated embodiment, the screen 38 includes an array of similarly sized holes sized to allow blood and small particles to pass through, but to prevent the passage of larger bone fragments that may be utilized as part of a bone graft procedure. In the illustrated embodiment, the array is formed of four similar quadrants. In other embodiments, the hole size may vary, the pattern of holes be changed, and different arrangements of holes may be used. In the illustrated embodiment, the insertion portion 36 is formed from a single piece of stainless steel to help reduce the number of crevasses and other locations where contaminants may collect.

Figure 7:
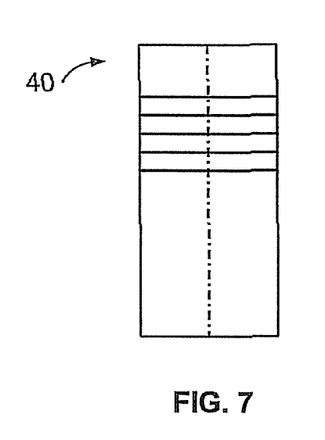
FIG. 7 illustrates a side view of a tube formed in accordance with an embodiment of the present invention.
Figure 8:
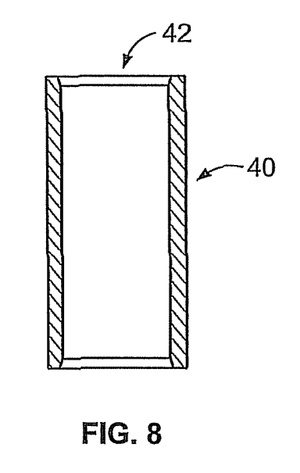
FIG. 8 provides a sectional view of the tube of FIG. 7.

FIG. 7 illustrates a side view of a tube 40 formed in accordance with an embodiment of the present invention, and FIG. 8 provides a sectional view of the tube 40. In the illustrated embodiment, the tube 40 is generally cylindrically shaped. In other embodiments, the tube (and components configured to be used the tube) may have a different cross-sectional shape, such as, for example, square, hexagonal, or octagonal. In the illustrated embodiment, the tube 40 includes a bore 42. The bore 42 generally extends along the length of the tube 40. The bore 42 may include chamfers at the top and bottom edges of the tube 40 to ease insertion of the various components. The bore 42 is sized to accept the insertion portions of the various components with a fluid-tight fit to help prevent or minimize any leakage that could impede the suction of bone and/or other materials through the bone collection system 10. The tube 40 is sized so that it can accept and retain a desired quantity of bone fragments in a lower portion (that portion of the tube between the base 50 and the screen 38 of the plunger 30).

Figure 9:
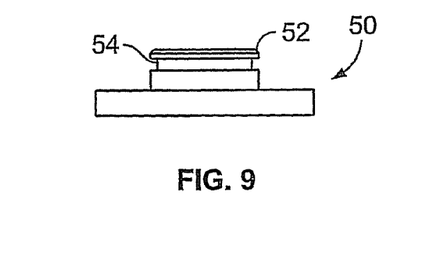
FIG. 9 illustrates a side view of a base formed in accordance with an embodiment of the present invention.

FIG. 9 illustrates a side view of a base 50 formed in accordance with an embodiment of the present invention. The base 50 includes an insertion portion 52. The insertion portion 52 includes a groove 54 that accepts an O-ring or seal (not shown) to prevent or minimize any leakage between the outer surface of the insertion portion 52 and the inner surface of the tube 40. In alternate embodiments, the insertion portion of the base and tube may be for example, snappably engageable, or, as another example, threadedly engageable. The base 56 may also include mounting holes so that the base 50 may be mounted to a frame or other structure during the procedure.

Figure 10:
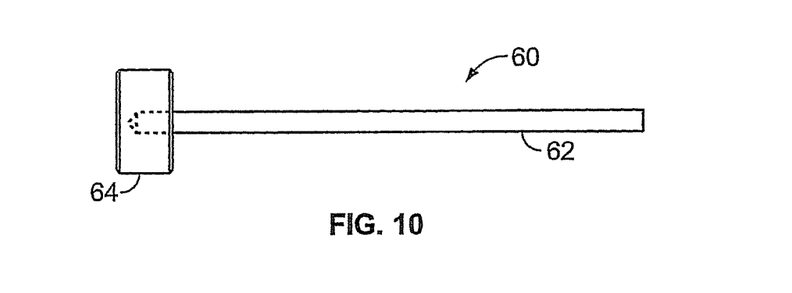
FIG. 10 illustrates a side view of a stylette formed in accordance with an embodiment of the present invention.

FIG. 10 illustrates a side view of a stylette 60 formed in accordance with an embodiment of the present invention. The stylette 60 includes a rod 62 and a head 64. The stylette 60 is configured to be used to force collected material out of the tube 40. In the illustrated embodiment, the head 64 of the stylette 60 is generally disc-shaped and sized to be accepted with minimal clearance by the tube 40, so that the head 64 may be slid along the length of the tube 40 to force material including collected bone fragments out of the tube 40 and to prevent or minimize any material from being caught between the outer surface of the head 64 and the inner surface of the tube 40, or leaking between those surfaces. The head 64 may also include a flexible wiper (not shown) around its outer edge to help minimize or eliminate any such leaking. In the illustrated embodiment, the tube 40 is generally symmetric, so the stylette 60 may be used to force the collected bone material out of either open end of the tube 40. In certain embodiments, the tube 40 may not have similarly sized open ends, and the stylette 60 may be configured to force material out only through one end.

Figure 11:
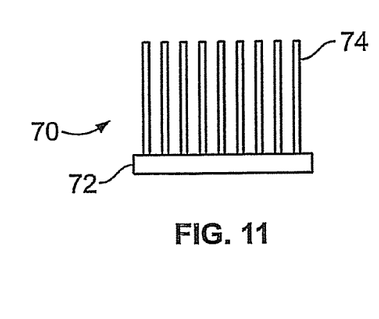
FIG. 11 illustrates a side view of a screen cleaner formed in accordance with an embodiment of the present invention.
Figure 12:
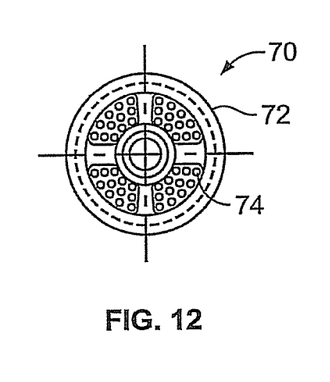
FIG. 12 illustrates a top view of the screen cleaner of FIG. 11.

FIG. 11 illustrates a side view of a screen cleaner 70 framed in accordance with an embodiment of the present invention, and FIG. 12 illustrates a top view of the screen cleaner 70. The screen cleaner 70 includes a base 72 and posts 74. The posts 74 are sized and formed in an array that corresponds to the array of holes in the screen of the plunger. The posts 74 are sized so that they may be accepted by the holes, and the posts 74 are used to force out of the screen particles or other material that may have accumulated in the holes of the screen. In the illustrated embodiment, the screen cleaner 70 is shaped as a ring that can slide over the plunger so that the posts 74 may be accepted by the holes of the screen. In certain embodiments, the screen cleaner 70 may include a post-shaped handle (or handles) or a sleeve-shaped handle that allows the screen cleaner 70 to be used while the plunger is in place in the tube. In certain embodiments, where the array of the screen is arranged in identical quadrants, the screen cleaner 70 may be sized and configured as a pie-shaped piece to clean one quadrant, or a portion of a quadrant, at a time. Further, in certain embodiments, the posts of the cleaner and holes of the screen are sized and configured such that the posts are snappably accepted by the holes so that the cleaner may be releasably secured to the screen. In certain embodiments, a stiff brush, for example, may be used additionally or alternatively to such a cleaner.

Returning to FIGS. 1 and 2, the assembly and operation of the illustrated bone collection system 10 will be further detailed. The base 50 is slid into one end of the tube 40, insertion portion 52 first, so that the base 50 is releasably secured to the tube 40 and provides a seal with the tube 40. Next the plunger 30 is slid into the other end of the tube 40, insertion portion 36 first, so that the tube 40 defines two chambers, a first chamber 80 (the lower portion in FIG. 2), and a second chamber 90 (the upper portion in FIG. 2), separated by the insertion portion 36 of the plunger 30. Next, the manifold 20 is slid into place over the plunger 30 and, insertion portion 28 first, into the tube 40, so that the manifold is releasably secured to the tube 40, and provides a seal with both the tube 40 and the plunger 30. The first chamber 80 is in direct fluid communication with the bore 32 of the plunger 30, and the second chamber 90 is in direct fluid communication with the outlet 24 of the manifold 20. The first chamber 80 is in fluid communication with the second chamber 90 via the holes in the screen 38 of the plunger 30. Thus, material collected from a patient by a collection device may be first drawn, by an external suction source applied to the outlet 24 of the manifold 20, through the bore 32 of the plunger 30 into the first chamber 80, through the screen 38 into the second chamber 90, and then through the outlet 24 of the manifold 20, from where it can be disposed. Larger, usable bone fragments are stopped by the screen 38 and accumulate in the first chamber 80. The plunger 36 may be adjusted along the length of the tube 40 to adjust the size of the first chamber 80 as desired.

Once a desired amount of collected fragments has been collected, the external suction device may be turned off, and the bone collection system 10 detached from the collection device and the external suction source. In certain embodiments, the manifold 20, plunger 30, and base 50 may be removed from the tube 40, and the stylette 60 introduced, head 64 first, to force the collected bone fragments out of one end and into a collection dish or reservoir to be added to a bone graft. In certain embodiments, the manifold 20 and plunger 30 may be removed, with the base 50 left in place. Additional bone graft material may be added to the bone fragments to create a mixture. The base 50 may then be removed, and the stylette 60 introduced, head 64 first, to force the mixture out of one end of the tube 40 to, for example, a dish or other reservoir, or, as another example, to a funnel that provides the material to a site of interest, such as a volume in an intervertebral space surrounding a spinal implant. The cleaner 70 may be used optionally as desired, at different times during the use of the bone collection system 10 to remove particles from the screen 38. Such particles may either be added to the collected bone fragments, if they are re-usable bone fragments, or discarded, as appropriate.

Figure 13:
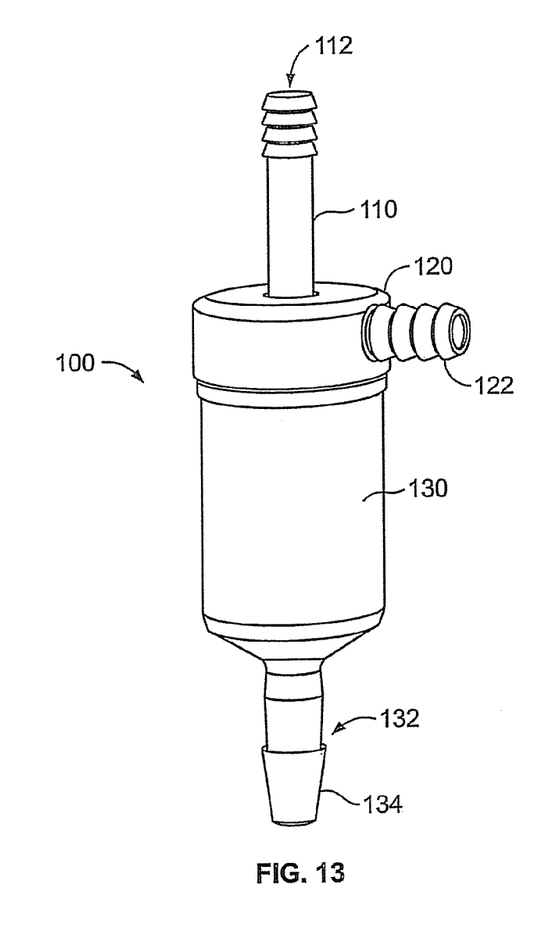
FIG. 13 illustrates a side view of a bone collection system formed in accordance with an embodiment of the present invention.
Figure 14:
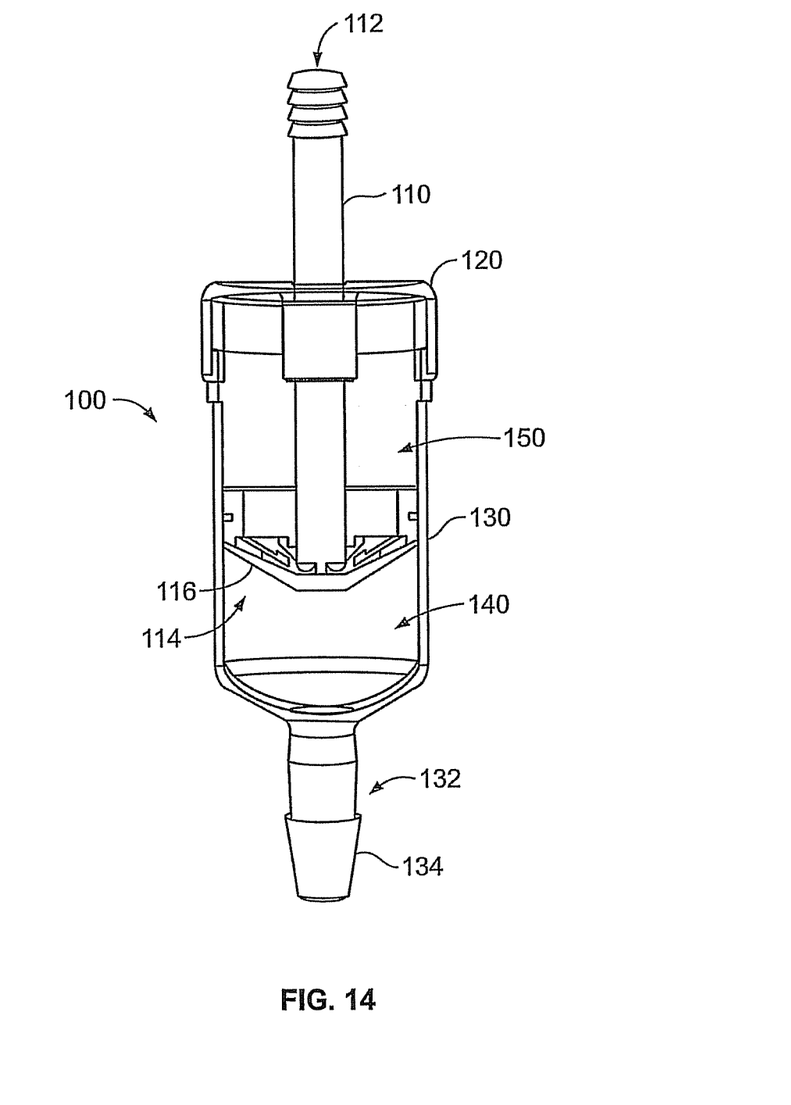
FIG. 14 illustrates a sectional view of the bone collection system of FIG. 13.

FIG. 13 illustrates a side view of a bone collection system 100 formed in accordance with an embodiment of the present invention, and FIG. 14 illustrates a sectional view of the bone collection system 100. The bone collection system 100 illustrated in FIGS. 13 and 14 may be similar to the previously discussed embodiments in many ways. The bone collection system 100 includes a plunger 110 with a bore 112, as well as a manifold 120 with an outlet 122. The bone collection system 100 also includes a tube 130 that may be divided into a first chamber 140 and a second chamber 150. The plunger 110 includes an insertion portion 114 having a screen 116. The screen 116 may also include an array of holes that act as a filter to retain re-usable bone fragments in the first chamber 140.

The insertion portion 114 of the plunger 110 of the embodiment illustrated in FIGS. 13-14 differs in certain respects from the insertion portion of the plunger of the embodiment illustrated in FIGS. 1-2. For example, the leading edge of the insertion portion 114 is fainted having a taper, instead of a substantially flat leading edge. A stylette (not shown) for the bone collection system 100 may have a similarly shaped taper. In other embodiments, only one of the plunger or stylette may have the tapered leading edge, or the two may have differently tapered leading edges.

In the illustrated embodiment, the tube 130 includes a tube outlet 132 formed as part of one of its ends. In other embodiments, such an outlet may be releasably secured to the base, such as, for example, by snapping, sliding, or by a threaded engagement. In the illustrated embodiment, the tube outlet 132 has a reduced diameter compared to the body of the tube 130, and accepts a cap 134. The reduced size of the tube outlet 132 allows for greater control and precision in applying mixture expelled from the tube 130. The cap 134 is releasably secured to the tube outlet 132 by, for example, snapping, sliding, or threading. The cap 134 is configured to be secured in place during bone collection, but to be easily removable once bone collection is complete.

Assembly and use of the bone collection system 130 may be generally similar in certain respects to assembly and use of the bone collection system 10. The cap 134 may be secured to the tube outlet 132. Next, the plunger 110 is positioned in the tube 130, insertion portion 114 first. The manifold 120 is then positioned over the plunger 110 and into the tube 130, and the bone collection system 130 coupled to a collection device and an external suction source. Thus, material from the harvest site may be suctioned through the bore 112 of the plunger 110 and into the first chamber 140, from the first chamber 140 through the screen 116 to the second chamber 150, and then out of the outlet 122 of the manifold 120, with re-usable bone fragments collected in the first chamber 140.

Next, the bone collection system 100 is de-coupled from the collection device and external suction source. Then, the plunger 110 and manifold 120 are removed. If desired, additional bone graft material may be added to the tube 130 for mixture with the collected bone fragments. Then, the stylette may be introduced and the cap 134 removed. Advancing the stylette into the tube 130 then forces the mixed bone graft material out of the tube outlet 132 in a generally controlled, precise fashion.

In certain embodiments, the bone graft material may be ejected from the tube into a dish or other reservoir for further mixing and/or later addition to a site of interest. In certain embodiments, the bone graft material may be ejected from the tube directly to a site of interest. For example, the bone graft material may be ejected from the tube directly to a space surrounding a spinal implant. In such embodiments, the tube outlet 132 may include a notch or other feature to help align the tube outlet 132 with a portion of an implanted spacer.

Figure 15:
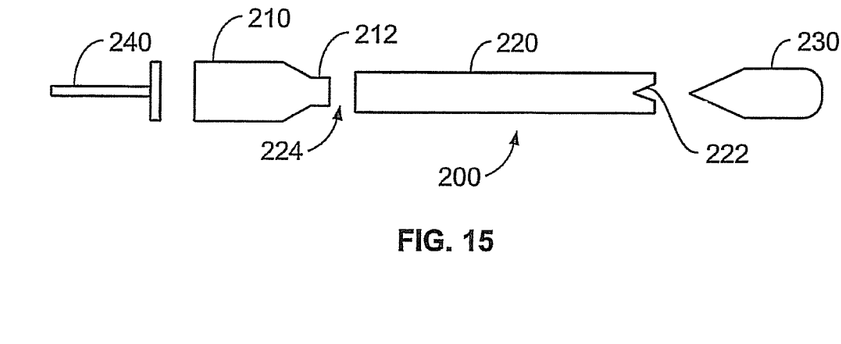
FIG. 15 provides a plan view of a bone collection and implant system formed in accordance with an embodiment of the present invention.

In certain embodiments, the bone collection system 100 may be part of a bone collection and implant system that also includes an implantable spacer and a funnel. Once a spacer is positioned in an intervertebral space as desired, the funnel may be coupled to the spacer. FIG. 15 provides a plan view of a bone collection and implant system 200 formed in accordance with an embodiment of the present invention. The system 200 includes a bone collection device 210 (which may be generally similar to the above described embodiments), a funnel 220, a spacer 230, and a stylette 240. The funnel 220 includes a notch 222 at one end that is configured to align the funnel 220 with the spacer 230 when the spacer 230 is in place in a patient, so that material passed through the funnel may be delivered to help fill a space or spaces surrounding the implant with bone graft material. The funnel 220 includes a bore 224 sized to accept a tube outlet 212 of the collection device 210. In some embodiments, the tube outlet has a reduced diameter compared to the diameter of the tube body, while in other embodiments the diameter of the tube outlet may be substantially the same as that of the tube. Advancing the stylette 240 of the bone collection device 210 advances bone graft material through the bone collection device 210, and then through the funnel 220 to be distributed around the spacer 230.

Figure 16:
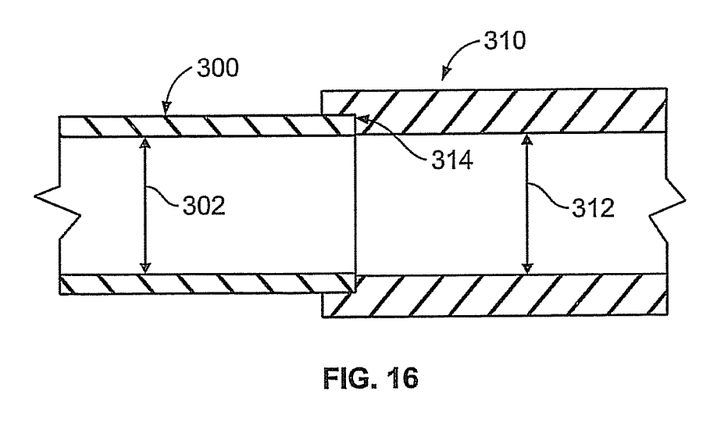
FIG. 16 illustrates a sectional view of a tube of a bone collection device and a funnel formed in accordance with an embodiment of the present invention.

FIG. 16 illustrates a sectional view of a tube 300 and a funnel 310 formed in accordance with an embodiment of the present invention. The tube 300 includes an inner diameter 302, and the funnel 310 includes an inner diameter 312. The funnel 310 includes a lip 314 that accepts the tube 300. The inner diameters 302, 312 are sized to be substantially similar so that a single stylette may be slidingly accepted by the funnel 310 and the tube 300, and such a stylette may be used to advance material through both the tube 300 and funnel 310. In certain embodiments, the funnel may be sized to match a tube outlet having a reduced diameter instead of the tube itself. In certain embodiments, the tube and funnel may present stepped, decreasing diameters so that different stylettes having different head sizes may be used as material is advanced along the tube-funnel combination.

Figure 17:
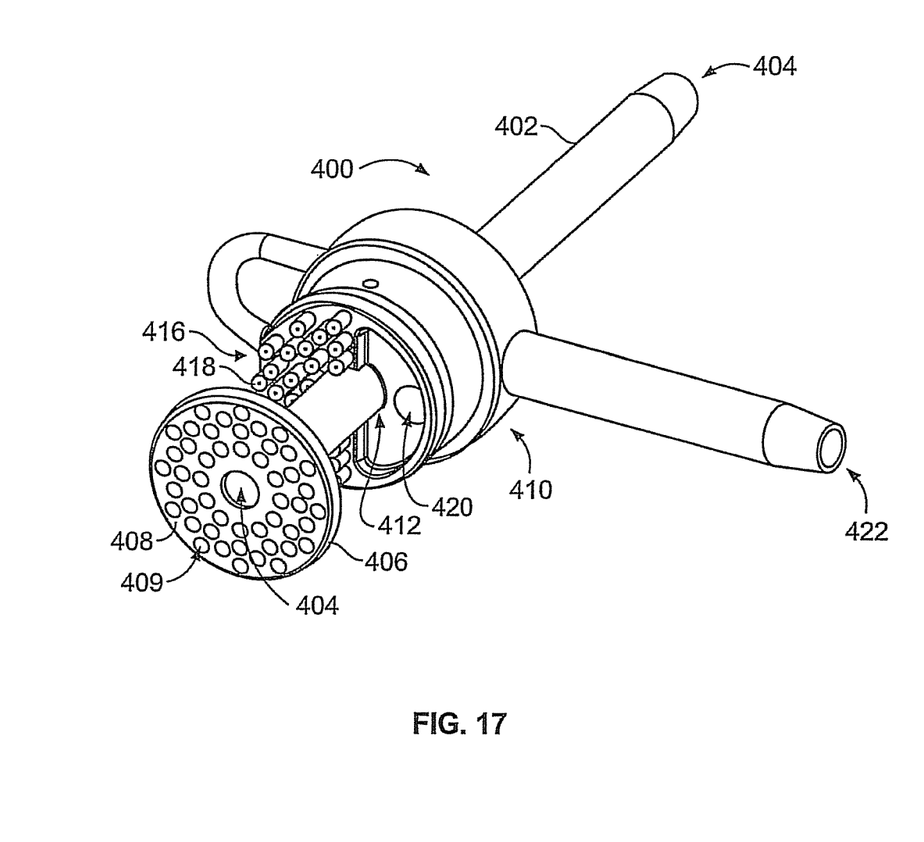
FIG. 17 illustrates a perspective view of a plunger and a manifold formed in accordance with an embodiment of the present invention.
Figure 18:
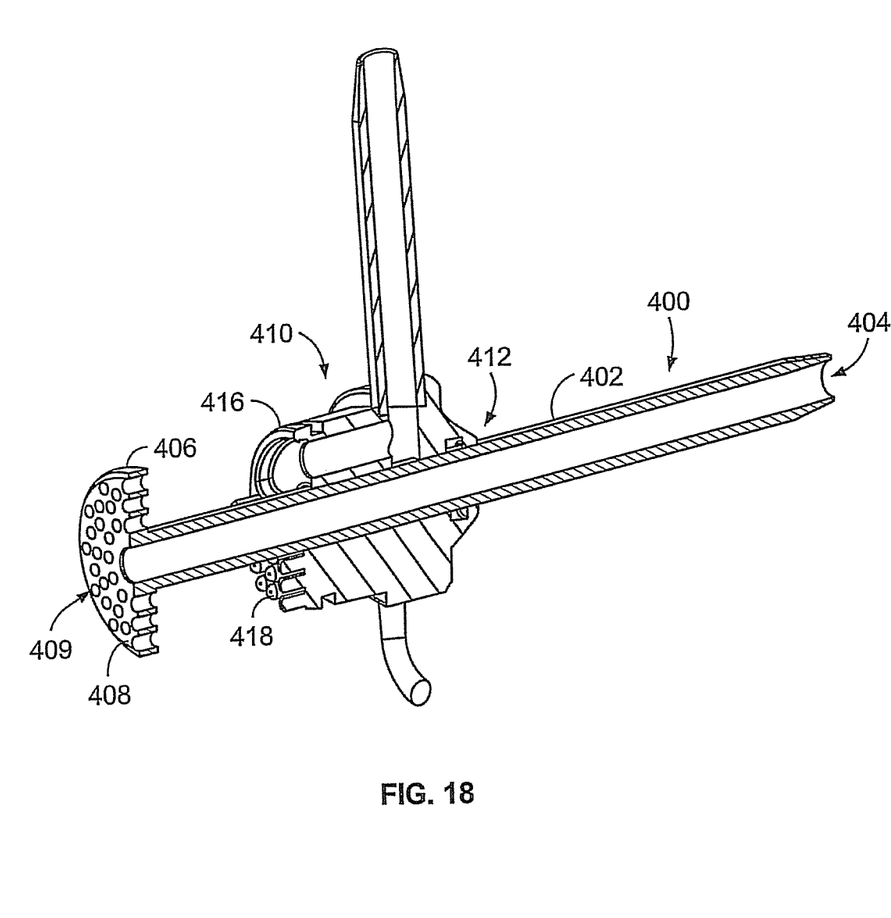
FIG. 18 illustrates a sectional view of the plunger and manifold of FIG. 17.

FIG. 17 illustrates a perspective view of a plunger 400 and a manifold 410 formed in accordance with an embodiment of the present invention, and FIG. 18 illustrates a sectional view of the plunger 400 and manifold 410. The plunger 400 and manifold 410 may be substantially similar in many respects to the above described embodiments. In the embodiment illustrated in FIGS. 17 and 18, the screen cleaner is incorporated into a portion of the manifold.

In the illustrated embodiments, the plunger 400 includes a shaft 402 with a bore 404 therethrough. The plunger 400 also includes an insertion end 406 adapted for insertion into a tube. The insertion end 406 includes a filter. In the illustrated embodiment, the filter includes a screen 408 that includes a plurality of holes 409. The holes 409 are sized to allow blood to pass through the screen but to not allow a desired size of bone fragment to pass.

The manifold 410 includes an opening 412 that is configured to accept the shaft 402 so that the manifold 410 and shaft 402 may be slid with respect to each other along the length of the shaft 402. A gasket or seal may be provided to prevent air and/or fluid leakage between the opening 412 and the shaft 402. Further, the manifold 410 includes a bottom portion 416 from which a plurality of posts 418 extend. The posts 418 extend toward the screen 408 when the manifold 410 is assembled on to the plunger 400. The posts 418 are sized and configured to be accepted by the holes 409, so that the posts 418 may be pressed through the holes 409 to clear debris from the holes 409 and un-clog the screen 408. The posts may form a complete array that matches an array of holes, or in other embodiments, the posts may form a partial array that matches a portion of the array of holes, wherein the manifold may be rotated about the shaft so that the partial array of posts may be selectively used to clear a portion of the array of holes, or may be used to clear the entire array a portion at a time. For example, in the illustrated embodiment, the posts 418 are configured so that they leave a cleared area proximal to an outlet hole 420 in the manifold 410 that leads to the outlet 422. The posts may be of a uniform height, or may be of varying height for convenience in insertion into obstructed holes.

Thus, the manifold 410 may be actuated along the shaft 402 such that the manifold 410 and screen 408 are slid toward each other. For example, when a filtering system is in an assembled condition with the manifold in place in the tube, the plunger may be retracted, or pulled up the tube toward the manifold and into contact with the manifold so that the posts enter and clear the holes of debris. The posts help force the debris into the tube with other harvested bone fragments. As another example, with the filtering system disassembled such that the manifold and plunger are removed from the tube, the manifold may be slid down the shaft of the plunger into contact with the screen such that the posts enter and clear the holes.

In certain embodiments of the present invention, a kit is provided including a bone collection device, a variety of sizes and/or types of funnels, and/or a variety of sizes and/or types of spacers to accommodate different patients and procedures.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A bone collection system including:
a plunger having a bore therethrough, an insertion portion, and an inlet, the inlet configured to accept material being harvested from a patient, the insertion portion including a filter configured to prevent passage of a desired size of bone fragment, the filter including a circular array of filter openings;
a tube configured to accept the insertion portion of the plunger wherein a first and a second chamber of the tube are defined, the first and second chambers being separated by the filter of the plunger; and
a manifold configured to be accepted by the tube, the manifold having an outlet configured to be accepted by an external suction source, wherein the inlet of the plunger is in fluid communication with the first chamber, the first and second chambers are in fluid communication through the filter, and the second chamber is in fluid communication with the outlet, wherein material being harvested from a patient may be drawn through the bone collection system and bone fragments of the desired size collected in the first chamber, the manifold further including a filter cleaner having a plurality of posts arranged in a partial array to engage a portion of the circular array of filter openings, the partial array of the plurality of posts leaving a cleared area proximate an outlet hole in communication with the outlet of the manifold.

2. A bone collection system according to claim 1, wherein the manifold is slidingly accepted by the plunger and the filter cleaner is located proximal to a bottom surface of the manifold, whereby the manifold and filter may be slid toward each other such that the plurality of filter openings in the filter accepts the plurality of posts in the filter cleaner of the manifold.

3. A bone collection system according to claim 1, wherein the manifold includes a manifold opening that is slidingly accepted by the plunger.

4. A bone collection system according to claim 1, wherein the tube includes a removable base for maintaining the material being harvested from the patient in the first chamber.

5. A bone collection system according to claim 1, further including a stylette configured to aid in the removal of material from the tube, the stylette including a head configured to be slidingly accepted by the tube.

6. A bone collection system according to claim 5, wherein the head of the stylette includes a tapered leading edge.

7. A bone collection system according to claim 1, wherein the plunger includes a tapered leading edge.

8. A bone collection system according to claim 1, wherein the tube includes a tube outlet proximal to an end of the tube, the tube outlet having a reduced diameter compared to the diameter of the tube.

9. A system for collecting and delivering bone material including:
a bone collection device including
a plunger having a bore therethrough, an insertion portion, and an inlet, the inlet configured to accept material being harvested from a patient, the insertion portion including a filter configured to prevent passage of a desired size of bone fragment, the filter including a circular array of filter openings;

a tube configured to accept the insertion portion of the plunger wherein a first and a second chamber of the tube are defined, the first and second chambers being separated by the filter of the plunger, the tube including a tube outlet;

a manifold configured to be accepted by the tube, the manifold having an outlet configured to be accepted by an external suction source, wherein the inlet of the plunger is in fluid communication with the first chamber, the first and second chambers are in fluid communication through the filter, and the second chamber is in fluid communication with the outlet, wherein material being harvested from a patient may be drawn through the bone collection device and bone fragments of the desired size may be collected in the first chamber, the manifold further including a filter cleaner having a plurality of posts arranged in a partial array to engage a portion of the circular array of filter openings, the partial array of the plurality of posts leaving a cleared area proximate an outlet hole in communication with the outlet of the manifold, the manifold further including a filter cleaner having a plurality of posts arranged in a partial array to engage a portion of the circular array of filter openings, the partial array of the plurality of posts leaving a cleared area proximate an outlet hole in communication with the outlet of the manifold;

a spacer configured for implantation in an intervertebral space;

a funnel configured for delivery of bone graft material to a space proximate to the spacer, the funnel including a tube end configured to be coupled to the tube outlet; and a stylette configured to be accepted by the tube and adapted to force collected bone fragments out of the tube outlet.

10. A system according to claim 9 wherein the funnel includes a spacer end opposite the tube end, the spacer end including a feature adapted for aligning the spacer end of the funnel with the spacer.

11. A system according to claim 9, wherein the manifold is slidingly accepted by the plunger and the filter cleaner is located proximal to a bottom surface of the manifold, whereby the manifold and filter cleaner may be slid toward each other such that a portion of the circular array of filter openings accepts the partial array of the plurality of posts of the filter cleaner.

12. A system according to claim 9, wherein the tube includes a removable base for maintaining the material being harvested from the patient in the first chamber.

13. A system according to claim 9, wherein the head of the stylette includes a tapered leading edge.

14. A system according to claim 9, wherein the plunger includes a tapered leading edge.

15. A system according to claim 9, wherein the tube outlet has a reduced diameter compared to the diameter of the tube.

16. A system according to claim 9, wherein the tube end of the funnel includes a lip sized to accept the tube outlet.

17. A system according to claim 9, wherein the funnel and the tube include substantially similar sized inner diameters, whereby a single stylette may be slidingly accepted by the funnel and the tube.

* * * * *